US009259266B2

(12) United States Patent
Schmaltz et al.

(10) Patent No.: US 9,259,266 B2
(45) Date of Patent: Feb. 16, 2016

(54) METHOD AND SYSTEM FOR STERILIZING AN ELECTROSURGICAL INSTRUMENT

(71) Applicant: COVIDIEN LP, Mansfield, MA (US)

(72) Inventors: Dale F. Schmaltz, Fort Collins, CO (US); Victor K. Appel, Longmont, CO (US); Paul Guerra, Los Gatos, CA (US)

(73) Assignee: Covidien LP, Mansfield, MA (US)

( * ) Notice: Subject to any disclaimer, the term of this patent is extended or adjusted under 35 U.S.C. 154(b) by 76 days.

(21) Appl. No.: 14/149,343

(22) Filed: Jan. 7, 2014

(65) Prior Publication Data

US 2014/0121661 A1 May 1, 2014

Related U.S. Application Data

(62) Division of application No. 12/367,791, filed on Feb. 9, 2009, now Pat. No. 8,623,276.

(60) Provisional application No. 61/029,218, filed on Feb. 15, 2008.

(51) Int. Cl.
*A61B 18/18* (2006.01)
*A61B 18/14* (2006.01)
*A61B 17/29* (2006.01)
*A61B 19/00* (2006.01)
*A61B 17/32* (2006.01)

(52) U.S. Cl.
CPC .............. *A61B 18/1445* (2013.01); *A61B 17/29* (2013.01); *A61B 19/34* (2013.01); *A61B 17/320016* (2013.01); *A61B 2017/2901* (2013.01); *A61B 2017/2945* (2013.01); *A61B 2018/1432* (2013.01); *A61B 2019/4868* (2013.01)

(58) Field of Classification Search
CPC .............. A61B 18/1445; A61B 19/34; A61B 17/320016; A61B 2017/2901
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Rebecca E Eisenberg

(57) ABSTRACT

An apparatus and method for use in sterilizing a surgical instrument is provided. The apparatus includes a surgical instrument that includes a housing having a shaft extending therefrom. The shaft includes one or more grooves defined therein that extends at least partially along the length thereof. The one or more grooves is configured to allow a sterilant passage therethrough. The apparatus also includes a jacket that encloses the shaft and allows the sterilant to travel along the one or more grooves.

18 Claims, 9 Drawing Sheets

(56) References Cited

U.S. PATENT DOCUMENTS

| | | |
|---|---|---|
| D299,413 S | 1/1989 | DeCarolis |
| D343,453 S | 1/1994 | Noda |
| 5,314,682 A * | 5/1994 | Sweval et al. .......... 424/45 |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,499,992 A | 3/1996 | Meade et al. |
| 5,578,052 A * | 11/1996 | Koros et al. ............ 606/174 |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 2008/0058830 A1 * | 3/2008 | Cole et al. .............. 606/107 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 3627221 | 2/1988 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1281878 | 10/2005 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |

(56) References Cited

FOREIGN PATENT DOCUMENTS

| | | |
|---|---|---|
| WO | WO 2008/040483 | 4/2008 |
| WO | WO 2011/018154 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales—Product Literature; Dec. 31, 2000.
Johnson et al. "Evaluation of a Bipolar Electrothermal Vessel Sealing Device in Hemorrhoidectomy" Sales—Product Literature; Jan. 2004.
E. David Crawford "Evaluation of a New Vessel Sealing Device in Urologic Cancer Surgery" Sales—Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales—Product Literature 1999.
LigaSure Vessel Sealing System, the Seal of Confidence in General, Gynecologic, Urologic, and Laparaoscopic Surgery; Sales—Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales—Product Literature 2001.
Bergdahl et al. "Studies on Coagulation and the Development of an Automatic Computerized Bipolar Coagulator" J.Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales—Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul.-Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex". Sales—Product Literature 2000.
Jarrett et al., "Use of the LigaSure Vessel Sealing System for Peri-Hilar Vessels in Laparoscopic Nephrectomy" Sales—Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales—Product Literature 1999.

* cited by examiner

METHOD AND SYSTEM FOR STERILIZING AN ELECTROSURGICAL INSTRUMENT

CROSS-REFERENCE TO RELATED APPLICATIONS

The present application is a divisional application of U.S. patent application Ser. No. 12/367,791 filed by Schmaltz et al. on Feb. 9, 2009, now U.S. Pat. No. 8,623,276, which claims the benefit of priority to U.S. Provisional Application Ser. No. 61/029,218 filed Feb. 15, 2008, the entire contents of which is hereby incorporated by reference.

BACKGROUND

1. Technical Field

The following disclosure relates to an apparatus and method for sterilizing electrosurgical instruments and, more particularly, to an apparatus and method for sterilizing laparoscopic instruments.

2. Description of Related Art

Laparoscopic surgery generally requires deploying a laparoscopic instrument into a body cavity. Prior to the laparoscopic procedure, the laparoscopic instrument and components associated therewith must be sterilized.

Commonly employed methods of sterilizing laparoscopic instruments include pasteurization, which requires heating, traditional chemical methods, such as chamber methods, which require flooding a chamber with a sterilant, usually a mix of ethylene oxide (commonly referred to EtO) and other gases, and micro-dose methods, which require introducing a sterilant, such as EtO, to a specially designed device.

Pasteurization may be an effective method for sterilizing some, but not all, laparoscopic instruments; this is because heat applied during pasteurization may cause damage to some, if not all, the heat sensitive materials located on or attached to the laparoscopic instrument.

Traditional chemical methods (e.g., chamber methods) of sterilization may have drawbacks inherent to the use of large amounts of sterilant being released into a large space, some of which may include increased cost, increased production time and may require larger amounts of toxic processing. Although micro-dose methods alleviate some of the drawbacks associated with the chamber methods of sterilization, micro-dose methods of sterilization have drawbacks as well. For example, the micro-dose method of sterilization is suitable when a small amount of instruments need to be sterilized.

SUMMARY OF THE DISCLOSURE

Accordingly, the present disclosure is directed to an apparatus for use in sterilizing a surgical instrument. The surgical instrument includes a housing that has a shaft extending therefrom. The shaft includes one or more grooves defined therein which extends at least partially the length thereof. In one embodiment the shaft includes a plurality of grooves extending the entire length thereof disposed in a fixed spatial relation relative to each other. For example, the plurality of grooves may be disposed in a generally orthogonal relation to each other. In an embodiment, the plurality of grooves may have a depth of about 0.002" and a width of about 0.004". The one or more grooves provide a path for a sterilant and is configured to allow a sterilant passage therethrough to infuse and sterilize the housing. In an embodiment the sterilant includes ethylene oxide.

The apparatus also includes a jacket or coating that encloses the shaft. In an embodiment, the jacket or coating may be in the form of a shrink wrap that encloses the shaft and allows the sterilant to travel along the one or more groves. In an embodiment the shrink wrap is a heat shrink wrap.

The present disclosure is also directed to a method for sterilizing a surgical instrument. The method includes the steps of: providing the surgical instrument with a shaft. The shaft includes one or more grooves defined therein which extends at least partially along the length thereof. The method includes the step of enclosing the shaft with a shrink wrap. The method also includes the step of introducing a sterilant into the one or more grooves.

The method may further include the steps of introducing a sterilant into a sterilization apparatus and subjecting the shrink wrap to a final shrinking stage, wherein after the final shrinking stage is completed the shrink wrap forms a tight seal against the shaft.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 5A:
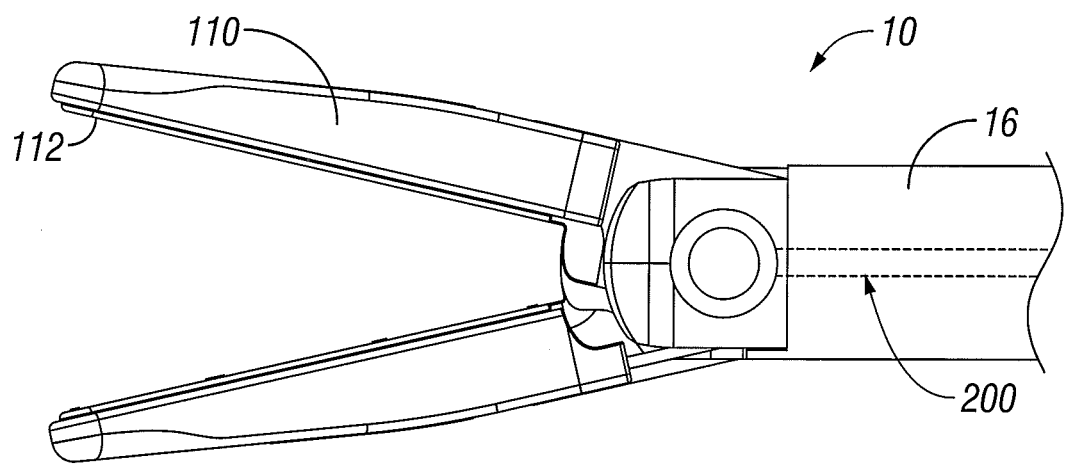
FIG. 5A is an enlarged, side view illustrating placement of a groove along the shaft of the forceps of FIG. 1 according to an embodiment of the present disclosure.
Figure 5B:
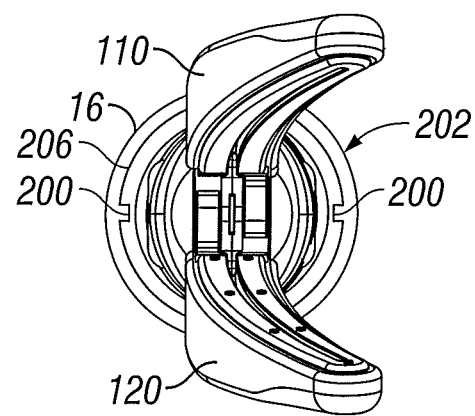
FIG. 5B is an enlarged, front view illustrating placement of grooves along the shaft of the forceps of FIG. 1 according to an embodiment of the present disclosure.

As mentioned above, laparoscopic instruments, like most surgical instruments, require sterilization before they can be introduced to a surgical site. Traditional chamber methods require placing a laparoscopic instrument into a chamber and flooding the chamber with a sterilant, which may include a mix of ethylene oxide (hereinafter EtO) and other gases. During the sterilization process the EtO and other gases enter the laparoscopic instrument and sterilize target areas and/or components, for example, those components internally located within the handle of the laparoscopic instrument (see FIG. 5A). However, due to the fact that the distal end of the shaft, which connects to an end effector of the laparoscopic instrument, may include a gasket, a heat shrink material, adhesive tape, rubber or other insulating boot or silicone, the sterilant may be impeded from entering the laparoscopic instrument in a timely fashion. Thus, in order to achieve an effective amount of sterilant at a target area more time is required in the sterilization apparatus. The shaft of the present disclosure, because of the unique groove and/or tunnel configuration defined therein, provides additional and/or alternate paths for the sterilant, thus facilitating the sterilant in reaching the target area.

The present disclosure relates to sterilizing laparoscopic instruments. As is known in the art, laparoscopic instruments generally include a handle assembly, a shaft, and an end effector assembly. Conventionally, the shaft is a long narrow generally circumferential tube having an outer and inner surface, which houses mechanical and electrical components that allow the handle and end effector to function as intended. The present disclosure includes a shaft that may include one or more grooves extending the length thereof (or partially along the length thereof), to be discussed in greater detail below. The one or more grooves are configured to provide a path for a sterilant. Additionally, there may be shrink wrap enclosing the shaft, which may allow the sterilant to travel along the grooves. Having a shaft configured in such a manner facilitates in the sterilization process of laparoscopic instruments.

Because the present disclosure is concerned with sterilizing, and not using, laparoscopic instruments, an in-depth, detailed description of the functioning features of laparoscopic instruments is not vital to the understandings of the present disclosure. In order for one skilled in the art to appreciate the sterilizing apparatus and method, as disclosed herein, only a brief description of two laparoscopic instruments now follows.

Figure 1:
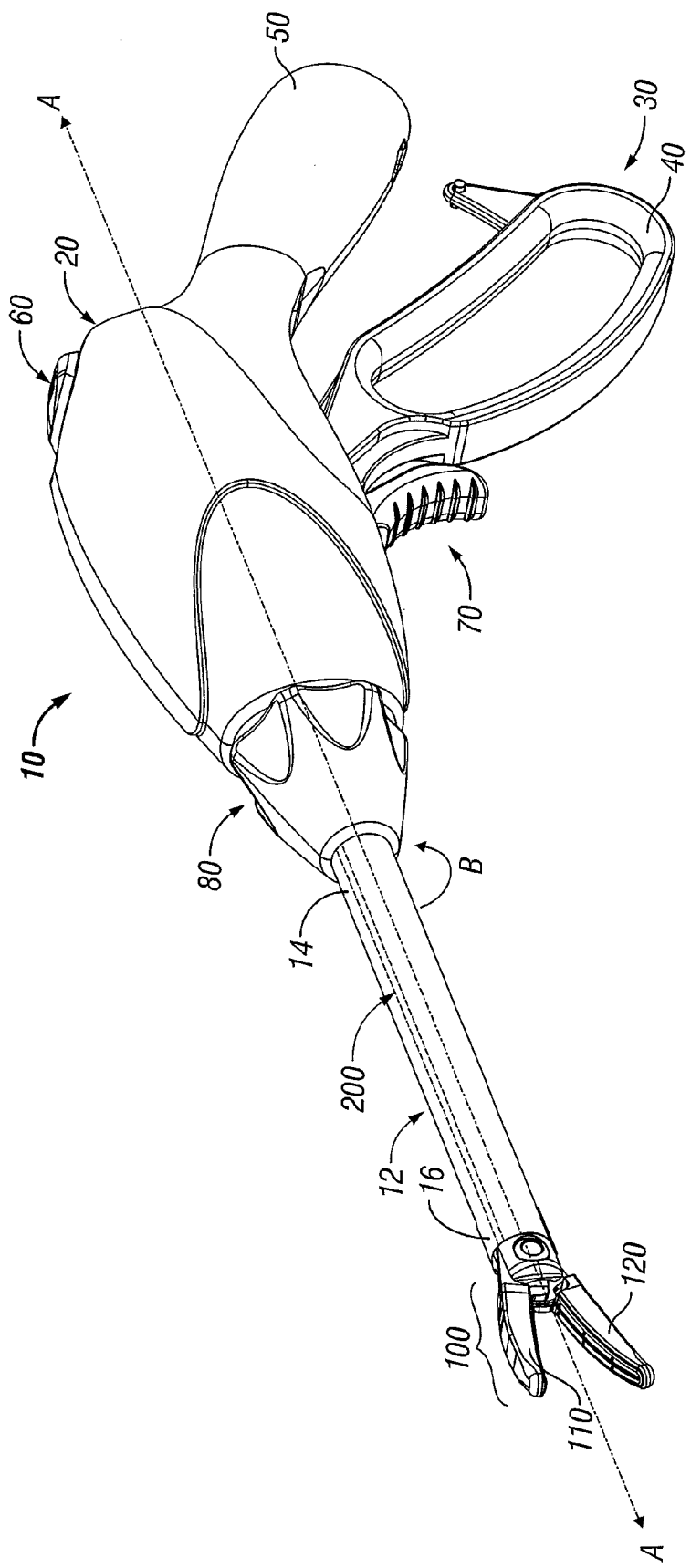
FIG. 1 is a perspective view of an endoscopic bipolar forceps shown in open configuration including a shaft having grooves, a handle assembly, a trigger assembly and an end effector assembly according to an embodiment of the present disclosure.
Figure 2:
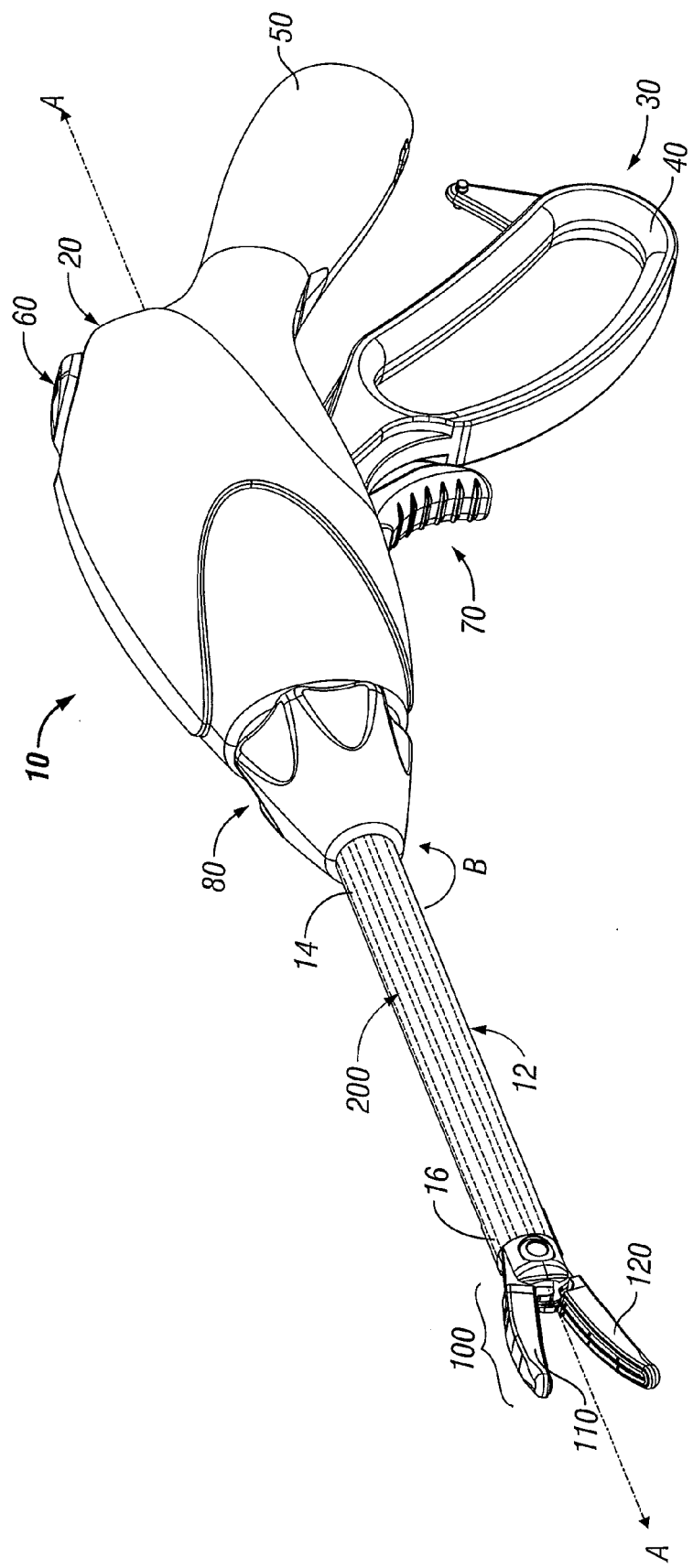
FIG. 2 is a front view of the forceps of FIG. 1 illustrating the shaft including a series of grooves defined thereon according to an embodiment of the present disclosure.

Turning now to FIG. 1, one embodiment of a laparoscopic instrument 10 is shown. For the remainder of the disclosure it will be assumed that the laparoscopic instrument is a bipolar forceps; keeping in mind that any laparoscopic instrument that includes a shaft may be employed with the present disclosure. Bipolar forceps 10 is shown for use with various electrosurgical procedures and generally includes a housing 20, a handle assembly 30, a rotating assembly 80, a trigger assembly 70 and an end effector assembly 100 which mutually cooperate to grasp, seal and divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument; however, an open version of the forceps may also include the same or similar operating components and features as described below.

Forceps 10 includes a shaft 12, to be described in greater detail below, which has a distal end 16 configured to mechanically engage the end effector assembly 100 and a proximal end 14 that mechanically engages the housing 20. In the drawings and in the descriptions that follow, the term "proximal," as is traditional, will refer to the end of the forceps 10 that is closer to the user, while the term "distal" will refer to the end that is farther from the user.

Figure 3:
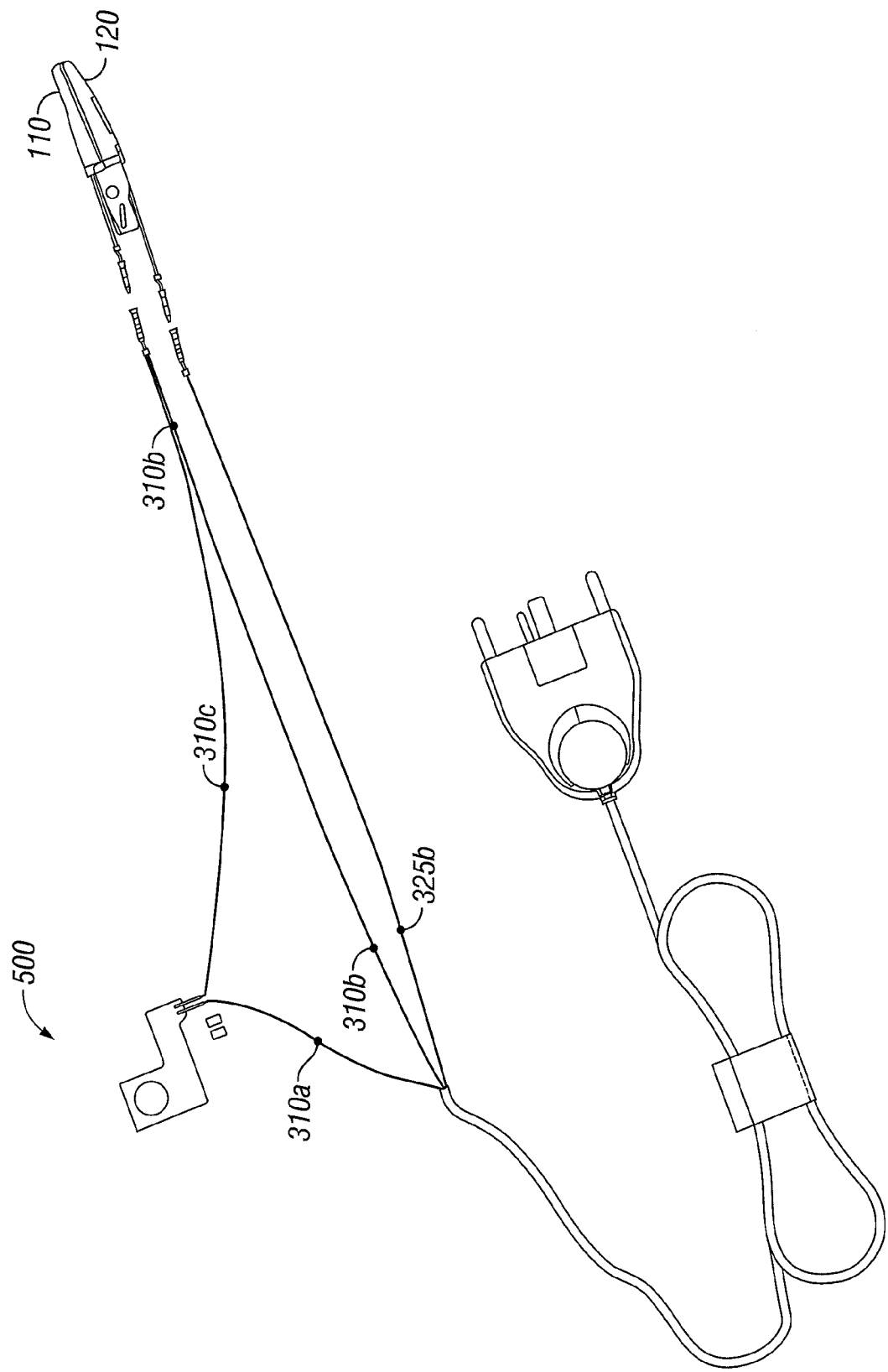
FIG. 3 is a schematic representation of the electrical configuration for the trigger assembly.

As best seen in FIG. 3, forceps 10 also includes an electrosurgical cable 310 which connects the forceps 10 to a source of electrosurgical energy, e.g., a generator 500 (shown schematically). It is contemplated that generators such as those sold by Valleylab—a division of Tyco Healthcare LP, located in Boulder Colo. may be used as a source of electrosurgical energy, e.g., Ligasure™ Generator, FORCE EZ™ Electrosurgical Generator, FORCE FX™ Electrosurgical Generator, FORCE 1C™, FORCE 2™ Generator, SurgiStat™ II or other suitable generators that may perform different or enhanced functions.

Cable 310 is internally divided into cable leads 310a, 310b and 325b which are designed to transmit electrical potentials through their respective feed paths through the forceps 10 to the end effector assembly 100. More particularly, cable feed 325b connects through the forceps housing 20 and through the rotating assembly to jaw member 120. Lead 310a connects to one side of the switch 60 and lead 310c connects to the opposite side of the switch 60 such that upon activation of the switch energy is transmitted from lead 310a to 310c. Lead 310c is spliced with lead 310b which connects through the rotating assembly to jaw member 110. Leads 310a-310c are but one example of the various internal components which need to be sterilized prior to use.

Handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Rotating assembly 80 is operatively associated with the housing 20 and is rotatable approximately 180 degrees about a longitudinal axis "A-A" (See FIG. 1).

As mentioned above, end effector assembly 100 is attached at the distal end 14 of shaft 12 and includes a pair of opposing jaw members 110 and 120. Movable handle 40 of handle assembly 30 is ultimately connected to a drive assembly 130 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Figure 4:
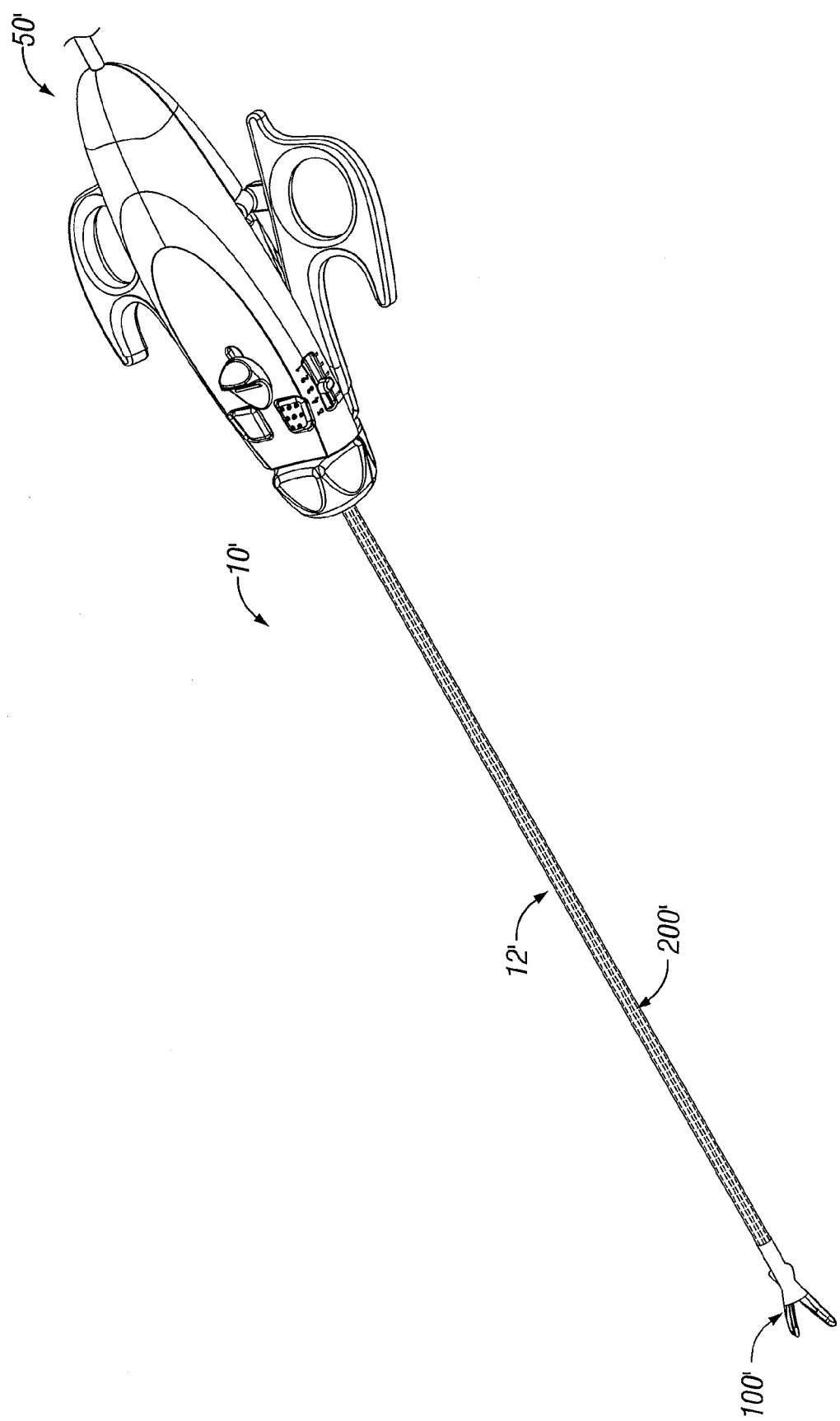
FIG. 4 is a perspective view of different endoscopic bipolar forceps shown in open configuration including a shaft having grooves, a handle assembly, a trigger assembly and an end effector assembly according to an embodiment of the present disclosure.

With reference to FIG. 4, another embodiment of a laparoscopic instrument 10' that may be employed with the present disclosure is shown. Laparoscopic instrument 10' also includes a handle 50', a shaft 12' and an effector assembly 100'. Shaft 12' of Forceps 10' includes a series of grooves 200' defined therealong which area configured to carry a sterilant to the various internal operating components thereof. Reference is made to U.S. patent application Ser. Nos. 11/595,194 and 11/540,335 for a more detailed explanation of the operation of both forceps 10 and 10', respectively.

For the remainder of the disclosure, and for the purposes of brevity, the apparatus and method for sterilizing a laparoscopic instrument will be described in greater detail with reference to laparoscopic instrument 10.

With reference to FIGS. 1, 2, 4, 5A, 5B, and 6A, illustrated in phantom are grooves 200 of shaft 12. The grooves 200 may be molded as part of shaft 12 during the manufacture process. In an alternate embodiment, at least one groove 200 may be machined out at a time after the manufacture of shaft 12.

Figure 6A:
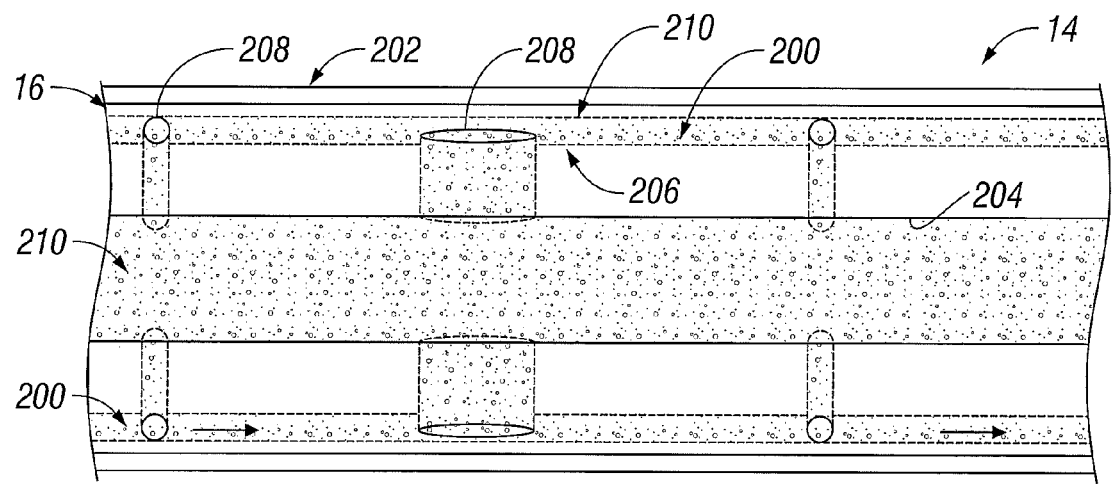
FIG. 6A is an enlarged, top view looking into the shafts of the forceps of FIGS. 1 and 4 illustrating one or more apertures or slits defined through the shaft according to an embodiment of the present disclosure.
Figure 6B:
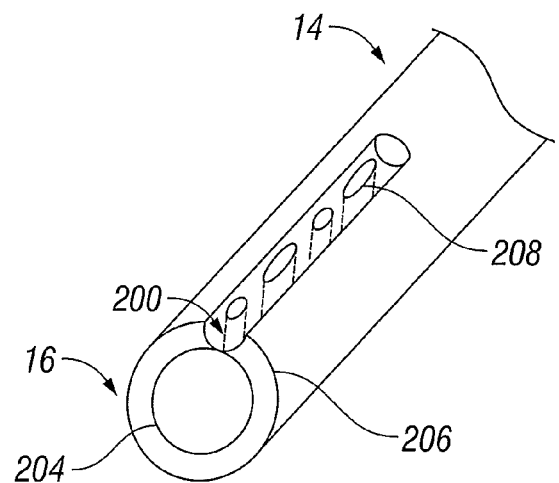
FIG. 6B is an enlarged, front perspective view of the shafts of the forceps of FIGS. 1 and 4 illustrating a groove extending partially the length of the shaft including apertures or slits defined through the shaft according to an embodiment of the present disclosure.
Figure 7:
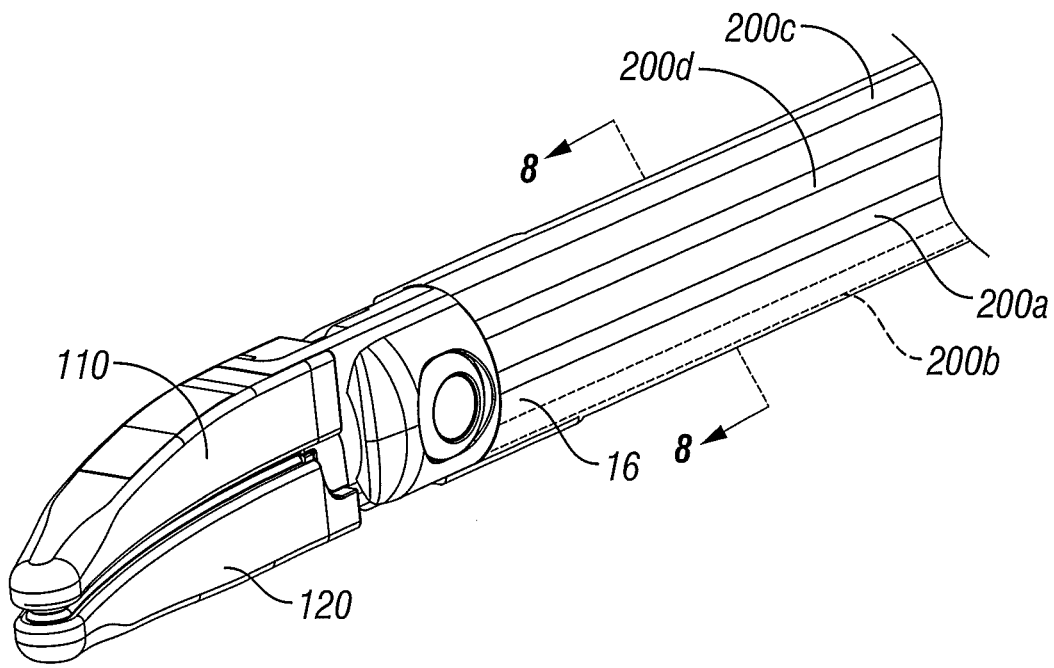
FIG. 7 is an enlarged, front perspective view of the shaft of the forceps of FIG. 1 having grooves defined in the shaft according to an embodiment of the present disclosure.

Similar to conventional shafts in the art, shaft 12 may be defined by inner and outer surfaces, 204 and 206, respectively, shown in FIG. 6B. In an embodiment, groove 200 may be located on outside surface 206 of shaft 12. Groove 200 of shaft 12 may include one or more apertures or slits 208 or any combination thereof extending from groove 200 to inside surface 204 of shaft 12, as illustrated in FIGS. 7A and 7B. Apertures 208 decrease the amount of time it takes for sterilant 210 to reach target areas within forceps 10. Apertures or slits 208 may be disposed anywhere within groove 200 and/or on shaft 12 of laparoscopic instrument 10. The shape and dimensions of apertures or slits 208 will depend on the needs of a user.

At least one groove 200 may extend from distal end 16 to proximal end 14 of shaft 12, as shown in FIG. 1. Having a groove 200 configured in this manner will allow sterilant 210 to travel from distal end 16 within groove 200 to proximal end 14, as shown in FIG. 6A and indicated by the arrow, wherein sterilant 210 may reach a target area, e.g., internal components of housing 20.

In an alternate embodiment, illustrated in FIG. 6B, groove 200 may extend from distal end 16 of shaft 12 a distance less than the length of shaft 12 to one or more apertures or slits 208 located within groove 200 of shaft 12. Having a shaft configured in this manner may allow the sterilizing agent to travel within groove 200 through aperture 208 into shaft 12, wherein sterilizing agent 210 may reach a specific target area.

With reference to FIGS. 2, 7, 8A-8B shaft 12 may be configured to include a plurality of grooves 200. For example, shaft 12 may include four grooves 200a-200d configured to extend the length of shaft 12. By providing four (or more) grooves 200a-200d more sterilant may travel along shaft 12 in less time, which may be beneficial for manufacturing purposes.

Figure 8A:
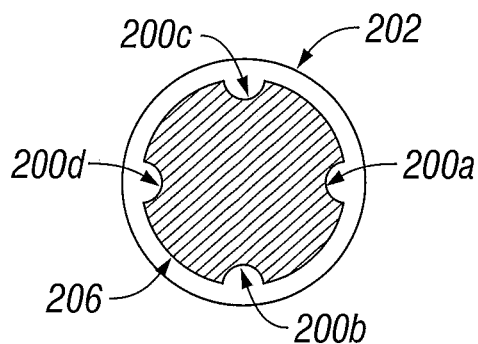
FIG. 8A is an enlarged, cross-sectional view taken along line 8-8 of FIG. 7 illustrating grooves having a generally arcuate shape.
Figure 8B:
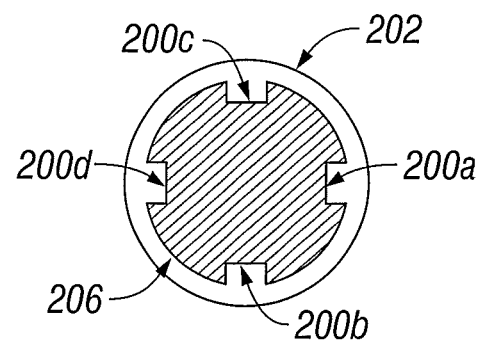
FIG. 8B is an enlarged, cross-sectional view similar to FIG. 8A illustrating grooves having a generally square shape.
Figure 9:
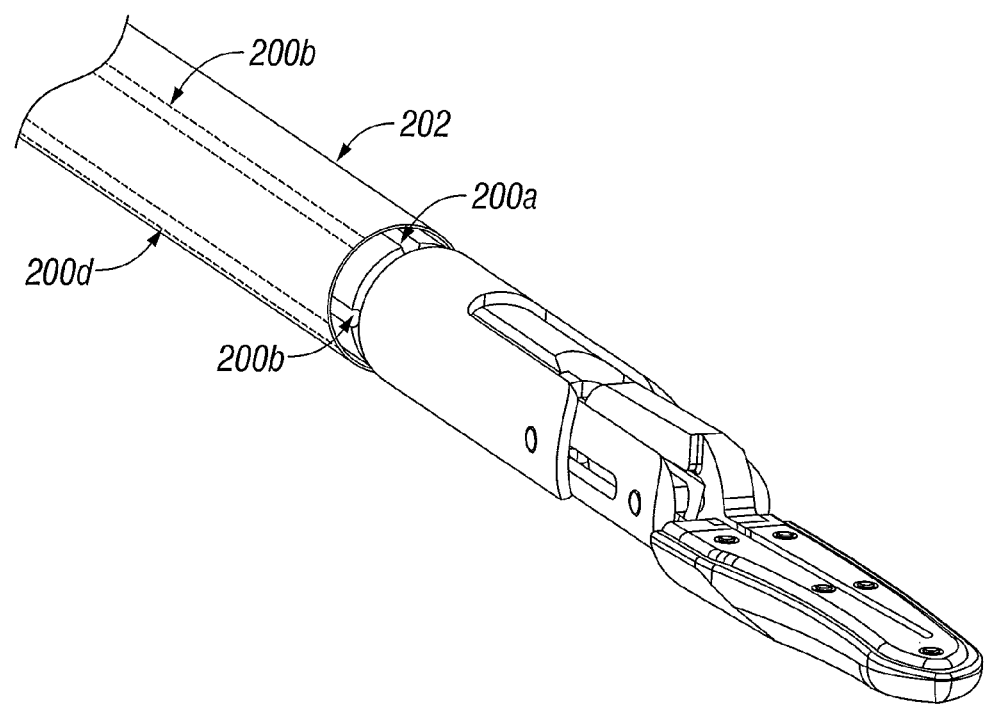
FIG. 9 is an enlarged, front perspective view illustrating a shrink wrap enclosing the shaft according to an embodiment of the present disclosure.

The four grooves 200a-200d may be disposed in a fixed spaced apart relation relative to one another on shaft 12. In one embodiment, the four grooves 200a-200d may be spaced apart at approximately 90° intervals, as shown in FIGS. 8A and 8B. It is envisioned that the four grooves 200a-200d may be disposed in other fixed spaced apart relations depending upon a particular purpose. For example, grooves 200a and 200b may be disposed at an angle X relative to each other, while the other two grooves 200c and 200d may be disposed at an angle Y from each other. The manner in which the four grooves 200a-200d may be disposed from each other may be depended on a particular forceps 10.

Grooves 200a-200d may have a generally arcuate cross-section, as seen in FIG. 8A or a square shape as illustrated in FIG. 8b. Other suitable shapes known in the art including but not limited to rectangular, triangular and the like may also be employed with grooves 200a-200d of the present disclosure. It is envisioned that the grooves 200 may each have their own unique shape.

With continued reference to FIGS. 8A and 8B the grooves 200 may have a depth of about 0.002" and a width of about 0.004". Other embodiments may include grooves 200a-200d with depths greater or less than 0.004" and widths greater or less than 0.002".

Figure 10:
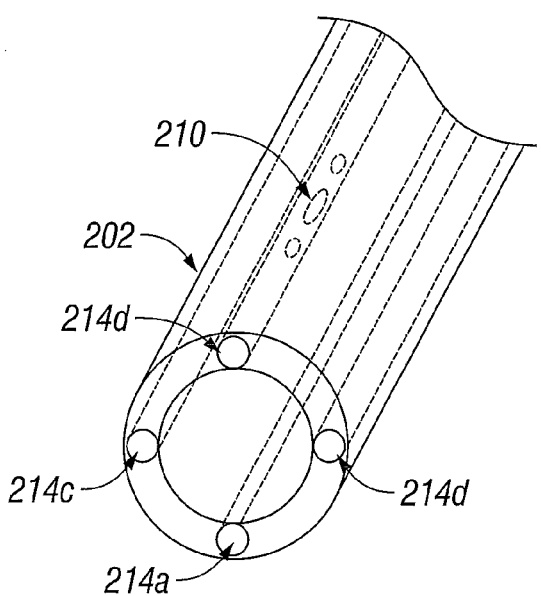
FIG. 10 is an enlarged, front perspective view of another envisioned embodiment having a shaft including tunnels defined therealong for carrying sterilization gas to the internal operating components of the forceps according to an embodiment of the present disclosure.
Figure 11:
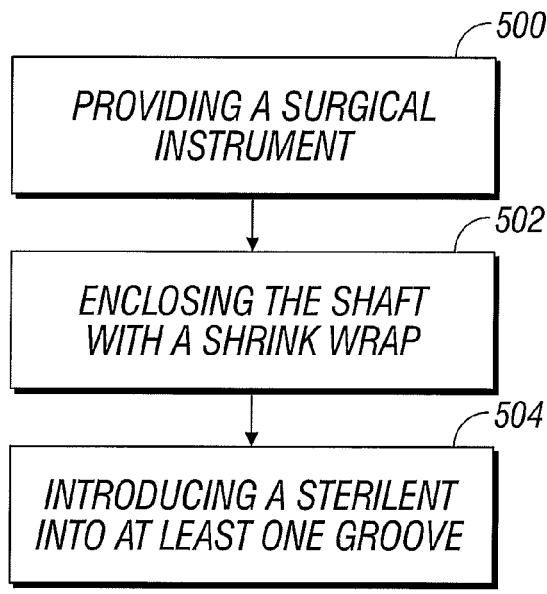
FIG. 11 is a flow chart illustrating a method according to an embodiment of the present disclosure.
Figure 12:
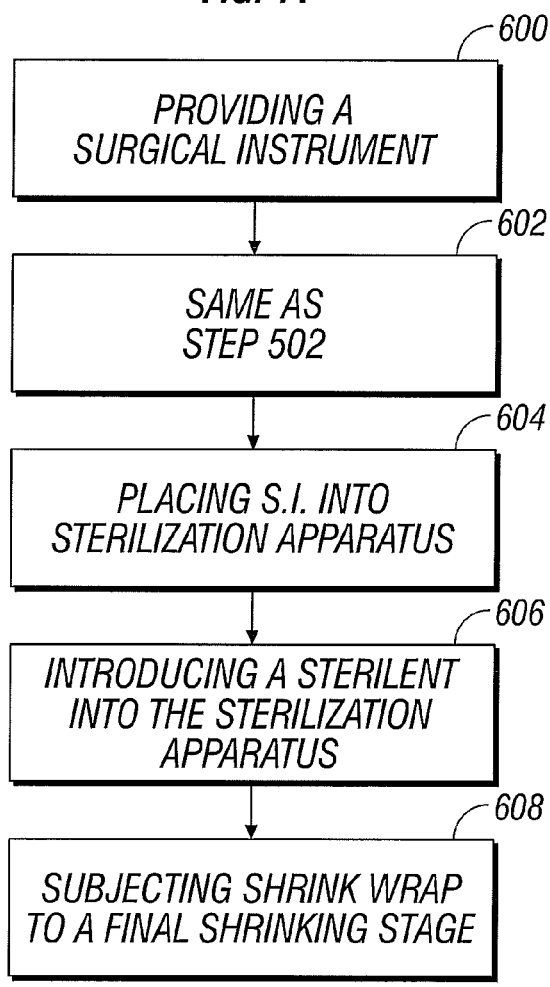
FIG. 12 is a flow chart illustrating a second method according to an embodiment of the present disclosure.

Referring now to FIG. 10, a jacket or coating 202 is shown enclosing shaft 12. In an embodiment, jacket 202 may be in the form of a shrink wrap or other suitable coating that encloses shaft 12 and allows sterilant 210 to travel along grooves 200a-200d. Shrink wrap 202 may be configured to enclose all of shaft 12 or only a portion thereof.

Shrink wrap 202 may be made from any suitable material known in the available art including any but not limited to polymer plastic film. Plastic films that can be employed as shrink wrap 202 may include polyethylene, PVC, and the like. Additionally, shrink wrap 202 may be configured for different clarities, shrink ratios, etc. Further, shrink wrap 202 may be of the kind that shrinks in one direction or multiple directions (e.g., unidirectional or bidirectional shrink wrap, respectively).

During the manufacturing process of bipolar forceps 10, shrink wrap 202 may be applied to shaft 12 by any suitable means known in the art. In an alternate embodiment, shrink wrap 202 may be applied and partially shrunk around shaft 12, the utility of having shrink wrap applied in this manner will be described in greater detail below.

One type of sterilant that is suitable for use with the present disclosure is EtO. As mentioned above, the EtO may be mixed with other gases during the sterilization process. Gases that may be used as dilutants may include but are not limited to CFCs and carbon dioxide.

In normal operation, prior to bipolar forceps 10 being introduced to a surgical site, bipolar forceps 10 must first be sterilized. As mentioned above, this may be accomplished by at least a couple of methods. For the purposes of the present disclosure it will be assumed bipolar forceps 10 is sterilized via sterilant EtO. As part of the sterilization process bipolar forceps 10 is placed in a sterilization chamber (not shown). Sterilant 210 is then introduced to the sterilization chamber via any suitable manner. As sterilant 210 is introduced to the sterilization chamber, sterilant 210 enters laparoscopic instrument 10 where it will reach target areas for sterilizing purposes, that is, the internal components associated with bipolar forceps 10. Having one or more grooves 200 provides additional paths for sterilant 210 to travel to the target area.

From the foregoing and with reference to the various figure drawings, those skilled in the art will appreciate that certain modifications can also be made to the present disclosure without departing from the scope of the same. For example, instead of employing one or more grooves 200, shaft 12 may include one or more tunnels 214 defined in shaft 12 or 12'. Tunnel 214 may be configured to function in a similar manner as described above with regard to groove 200. That is, one or more tunnels 214a-214d may extend the length shaft 12 (or at least partially thereof), the tunnels 214a-214d providing a path for a sterilant 210 to reach a target area (see FIG. 10). Tunnel 214 may include apertures or slits 208 as described above with reference to grooves 200.

The present disclosure also provides a method for sterilizing a laparoscopic instrument the method including the steps of: providing a laparoscopic instrument 10 including: a shaft 12 including one or more grooves 200a-200d extending at least partially the length thereof, the grooves providing a path for a sterilant; and providing a shrink wrap 202 enclosing the shaft and allowing the sterilant to travel along the grooves. The method also includes the steps of: placing the laparoscopic instrument into a sterilization apparatus; and introducing the sterilant into the sterilization apparatus for the purposes of sterilizing the laparoscopic instrument.

In one embodiment, heat shrink wrap 202 may be subjected to an initial shrinking stage, wherein heat shrink wrap 202 is not completely shrunk prior to placing laparoscopic instrument 10 into a sterilization apparatus. The sterilization apparatus may be configured to further shrink the shrink wrap 202. Conventional ways for shrinking heat wrap 202 may include a heat tunnel, heat gun, etc., which will not reach a temperature sufficient to cause damage to the internal components of the forceps 10. Thus, after laparoscopic instrument 10 is placed inside the sterilization apparatus and sterilant 210 is introduced, because shrink wrap 202 is not completely shrunk, sterilant may freely enter laparoscopic instrument 10 and reach a target area. The method may further include the step of: subjecting the shrink wrap to a final shrinking stage, wherein after the final shrinking stage is completed, the shrink wrap forms a tight seal against the shaft.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing; and
   a shaft extending distally from the housing and having an outer surface and an inner surface, the shaft including:
      at least one groove defined in the outer surface and extending at least partially along a length of the shaft; and
      at least one aperture disposed within the at least one groove and extending to the inner surface of the shaft, the at least one aperture configured to allow a sterilant to pass therethrough to target specific areas of the surgical instrument prone to contamination; and
   a jacket enclosing the shaft and configured to allow the sterilant to travel along the at least one groove.

2. The surgical instrument according to claim 1, wherein the at least one groove is a plurality of grooves that extend the entire length of the shaft, each groove of the plurality of grooves disposed in fixed spatial relation to each other.

3. The surgical instrument according to claim 2, wherein each groove of the plurality of grooves is disposed in general orthogonal relation to each other.

4. The surgical instrument according to claim 1, wherein the at least one groove has a depth of about 0.002 inches and a width of about 0.004 inches.

5. The surgical instrument according to claim 1, wherein the jacket is a heat shrink wrap.

6. The surgical instrument according to claim 5, wherein the heat shrink wrap is formed from a polymer plastic film.

7. The surgical instrument according to claim 1, wherein the sterilant includes ethylene oxide.

8. The surgical instrument according to claim 7, wherein the sterilant includes a mixture of ethylene oxide and one of chlorofluorocarbon or carbon dioxide.

9. The surgical instrument according to claim 1, wherein the at least one groove includes one of an arcuate or square cross-section.

10. The surgical instrument according to claim 1, wherein the at least one groove has a proximal end disposed within the housing.

11. A laparoscopic instrument, comprising:
    a housing; and
    a shaft extending distally from the housing and having an outer surface and an inner surface, the shaft including:
       at least one tunnel defined in the outer surface and extending at least partially along a length of the shaft; and
       at least one aperture disposed within the at least one tunnel and extending to the inner surface of the shaft, the at least one tunnel configured to allow a sterilant to pass therethrough to target specific areas of the surgical instrument prone to contamination; and
    a jacket enclosing the shaft and configured to allow the sterilant to travel along the at least one tunnel.

12. The laparoscopic instrument according to claim 11, wherein the at least one tunnel is a plurality of tunnels that extend the entire length of the shaft, each tunnel of the plurality of tunnels disposed in fixed spatial relation to each other.

13. The laparoscopic instrument according to claim 12, wherein each tunnel of the plurality of tunnels is disposed in general orthogonal relation to each other.

14. The laparoscopic instrument according to claim 11, wherein the jacket is a heat shrink wrap.

15. The laparoscopic instrument according to claim 14, wherein the heat shrink wrap is formed from a polymer plastic film.

16. The laparoscopic instrument according to claim 11, wherein the sterilant includes ethylene oxide.

17. The laparoscopic instrument according to claim 16, wherein the sterilant includes a mixture of ethylene oxide and one of chlorofluorocarbon or carbon dioxide.

18. The laparoscopic instrument according to claim 11, wherein the at least one tunnel has a proximal end disposed within the housing.

* * * * *